(12) United States Patent
Bachschmidt et al.

(10) Patent No.: US 9,974,490 B2
(45) Date of Patent: May 22, 2018

(54) METHOD AND DEVICE FOR SEGMENTING A MEDICAL EXAMINATION OBJECT WITH QUANTITATIVE MAGNETIC RESONANCE IMAGING

(71) Applicant: Siemens Aktiengesellschaft, Munich (DE)

(72) Inventors: Theresa Bachschmidt, Marloffstein (DE); David Grodzki, Erlangen (DE); Heiko Meyer, Uttenreuth (DE); Mathias Nittka, Baiersdorf (DE); Esther Raithel, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 225 days.

(21) Appl. No.: 14/956,755

(22) Filed: Dec. 2, 2015

(65) Prior Publication Data

US 2016/0155238 A1 Jun. 2, 2016

(30) Foreign Application Priority Data

Dec. 2, 2014 (DE) ........................ 10 2014 224 656

(51) Int. Cl.
*G06K 9/00* (2006.01)
*A61B 5/00* (2006.01)
*A61B 5/055* (2006.01)
*G01R 33/56* (2006.01)
*G06T 7/00* (2017.01)
(Continued)

(52) U.S. Cl.
CPC ............ *A61B 5/743* (2013.01); *A61B 5/0037* (2013.01); *A61B 5/055* (2013.01); *G01R 33/5608* (2013.01); *G06T 7/0014* (2013.01);
*G06T 7/11* (2017.01); *G06T 7/62* (2017.01); *A61B 2576/00* (2013.01); *G06T 2207/10088* (2013.01);
(Continued)

(58) Field of Classification Search
CPC ........ A61B 5/743; A61B 5/0037; A61B 5/055; G06T 7/62; G06T 7/0014; G06T 7/11; G06T 2207/10088; G01R 33/5608
USPC ........................................................ 382/131
See application file for complete search history.

(56) References Cited

U.S. PATENT DOCUMENTS

2007/0232889 A1 10/2007 Boese et al.
2008/0139920 A1* 6/2008 Biglieri .................. A61B 5/055
600/410

(Continued)

OTHER PUBLICATIONS

Fripp, et al. "Automatic Segmentation and Quantitative Analysis of the Articular Cartilages From Magnetic Resonance Images of the Knee". IEEE Transactions on Medical Imaging, vol. 29, No. 1, pp. 55-64 (2010).

(Continued)

*Primary Examiner* — Van D Huynh
(74) *Attorney, Agent, or Firm* — Schiff Hardin LLP

(57) ABSTRACT

In a method and magnetic resonance apparatus for segmenting image data of an examination object, raw data of the examination object are achieved with the operation of a magnetic resonance scanner. Quantitative image data of the examination object are then calculated in a processor from the raw data. At least one physical variable of the examination object is quantitatively ascertained pixelwise and is displayed. The quantitative image data are segmented for identification of predetermined objects in the quantitative image data, and displayed in a display unit.

17 Claims, 3 Drawing Sheets

(51) Int. Cl.
  *G06T 7/11*  (2017.01)
  *G06T 7/62*  (2017.01)
(52) U.S. Cl.
  CPC .............. *G06T 2207/20036* (2013.01); *G06T 2207/30008* (2013.01)

(56) References Cited

U.S. PATENT DOCUMENTS

2010/0127704 A1* 5/2010 Warntjes ................ G01R 33/56 324/309
2013/0265047 A1* 10/2013 Griswold ............... G01R 33/56 324/309

OTHER PUBLICATIONS

Ma et al. "Magnetic resonance fingerprinting", Nature 495,7440, pp. 187-192, (2013).
Deshmane, et.al.: "Validation of Tissue Characterization in Mixed Voxels Using MR Fingerprinting",: Proc. Intl. Soc. Mag. Reson. Med., vol. 22, p. 0094 (2014).

* cited by examiner

METHOD AND DEVICE FOR SEGMENTING A MEDICAL EXAMINATION OBJECT WITH QUANTITATIVE MAGNETIC RESONANCE IMAGING

BACKGROUND OF THE INVENTION

Field of the Invention

The invention concerns a method and a device for segmenting a medical examination object by the application of quantitative magnetic resonance (MR) imaging methods for medical issues and segmenting processes.

Description of the Prior Art

The significance of segmenting processes, i.e. the depiction of specific sections of examination objects, has increased greatly in the past years in MR imaging in general and in orthopedic MR imaging in particular. One application example is the segmenting of cartilage tissue and the subsequent automatic evaluation of thickness, volume, etc. to detect potential cartilage damage as early as possible and to objectively quantify a potential successful treatment or course over time of diseases (e.g. arthroses). Other areas are e.g. segmenting of tumors or vessel deposits. Segmenting methods are also used to depict bones or fluids or in MR PET attenuation correction. Current segmenting algorithms for structures having complex geometries, such as e.g. joints, are often computing-intensive and in particular in conventional MR images, which generate only one qualitative contrast, prone to error.

Current segmenting methods are based on one or more MR image data sets with a specific contrast weighting. The contrast of the image is generally chosen such that there is an optimally high contrast between the types of tissue to be segmented.

Segmenting algorithms must generally first of all learn the used contrast, for example by adjusting the choice of parameters or extraction of model parameters from training data, since, depending on the choice of protocol parameters, a different contrast may exist. Errors can occur during segmenting if the scan protocol is changed too much. In addition there is the compounding factor that the qualitative contrast of conventional MR images can vary from one MR system to another, from one used coil to another, and even from one day to another. Further image differences can occur due to the patient positioning and choice of coil, scan adjustments, noise level, manufacturer, SW versions, etc. To achieve more robustness modern segmenting algorithms often use prior knowledge about the shape of the structures to be segmented (atlases, shape models). The results of methods that use such qualitative data can turn out badly, however, as soon as a case deviates too much from the models obtained from training data (e.g. rare pathologies). In general a reproducible scan result and therewith reliable segmenting cannot always be guaranteed.

SUMMARY OF THE INVENTION

An object of the present invention is therefore to provide a method with which the drawbacks of the previously known segmenting methods can be avoided and thus provide a more accurate method, which can be reproduced better, for segmenting examination objects.

According to the invention this object is achieved by a method for segmenting image data of a medical examination object by at least one quantitatively measured physical variable and by a device for segmenting image data of a medical examination object by at least one quantitatively measured physical variable.

Firstly, the raw data are recorded by the MR signals of the examination object. The data are thereby available in unprocessed form for further analysis and therefore includes a comprehensive information content that can be used accordingly for further processing.

Quantitative image data of the examination object are also determined, wherein pixels respectively representing at least one physical variable of the examination object is quantitatively ascertained and displayed. The at least one physical variable is thus displayed pixel-by-pixel. The quantitative ascertainment of the physical variable has the advantage that, in contrast to qualitative data, the effect of disruptive scan conditions, such as different coils, scanners or patient positioning, is much smaller than in the ascertainment of qualitative variables.

In a further step the quantitative image data are segmented (e.g. based on atlases, shape models, or other segmenting approaches), in order to identify predetermined objects therein. Predetermined objects can be, for example, bones or tendons, or any type of organ or tissue structure. This type of segmenting can be used to ascertain optimally accurate identification of the physical structure of the object.

An advantage of this method is that better reproducibility of the quantitative image data and improved and more accurate segmenting of the predetermined objects can be achieved by scanning quantitative physical values.

In a further exemplary embodiment for segmenting image data of a medical examination object, in addition to the above-described method, after the ascertainment of first image data of the examination object, and the pixelwise quantitative ascertainment of the first physical variable and segmenting of the first quantitative image data, a first quality parameter is determined for the segmented first image data. This contains information on how reliably the predetermined objects in the segmented first image data can be identified.

Second image data are ascertained, and a second physical variable is quantitatively ascertained pixelwise, the second image data are segmented, and a second quality parameter is determined for the segmented second image data.

The segmented first quantitative image data are then compared with the segmented second quantitative image data, and in a region in which the identified objects in the segmented first quantitative image data do not match the identified objects in the segmented second quantitative image data, the quantitative image data whose associated quality parameter is greater are used for the identification of the predetermined objects.

Determining at least two different physical variables has the advantage that a predetermined object can be segmented more accurately because at least two physical variables can contain more information about the tissue of the predetermined object than one physical variable.

Furthermore, a computationally overlaid variable can be ascertained from the first and the second physical variables of the examination object. Improved segmenting can be achieved thereby because more accurate segmenting can be ascertained from the computational combination of the two physical variables.

In a further embodiment of the method the at least one physical variable in the quantitative image data of the predetermined object can be compared with a first reference database which comprises a large number of physical variables of examination objects. When a predefined deviation of the at least one physical variable is overshot, this overshooting can be displayed. It can therefore advantageously be achieved that predetermined objects are ascertained in which physical variables differ from the reference range.

It is also possible to determine, from the at least one physical variable in the quantitative image data, the volume of the predetermined object, and to compare that volume with a second reference database that includes a collection of volume data for each of a large number of examination objects. When a predefined deviation of the volume is overshot, an identification step for determining the volume deviation can take place.

After segmenting the objects in the quantitative image data, the objects in the image data of the predetermined object can likewise be segmented further by MR fingerprinting subvoxel quantification, wherein the at least one physical variable of the pixels is taken from the first reference database. A composition of an examination object can advantageously be determined more accurately, in this way.

Furthermore, in an embodiment of the method, after selection of a pixel in the quantitative image data, adjacent pixels are sought that, up to a defined deviation, have the same quantitative value as the selected pixel. The same quantitative values are allocated to the same tissue. In this method step a tissue region can therefore advantageously be ascertained which is allocated to a specific object.

In a further exemplary embodiment of the method, the predetermined objects can be ascertained by thresholding, correlation analysis, region growing methods, image processing methods in respect of active objects (active shape models) or statistical test methods of the at least two physical variables in the quantitative image data by comparison with the reference database. Pathological or degenerative changes can advantageously be ascertained in an early stage therefore.

In a further exemplary embodiment of the method the quantitative image data can be supplied to the first or second reference database. Additional data can therefore advantageously be provided from the data that already exists in the databases, which data can be used during the course of subsequent examinations to achieve additional accuracy in the evaluation of examination objects.

In a further exemplary embodiment, the quantitative image data can likewise be allocated to one tissue type and after its allocation be supplied together with this allocation to the first or second reference database.

In a further exemplary embodiment, a segmenting method can be carried out which uses inter alia a statistical model of the examination object, wherein at least one statistical variable of the at least one quantitatively ascertained physical variable is determined. The statistical model takes into account the at least one statistical variable. This has the advantage that the accuracy of the statistical model can be improved thereby.

In another embodiment of the method a quantitative ratio between at least two different physical variables of the predetermined object can be ascertained and be compared with a quantitative ratio of the two different physical variables from the first reference database. The deviation of the quantitative ratio from the reference database can be displayed made in the form of a graphic or as a color chart or as color overlays over medical images. The deviation can be visually displayed in relation to a reference model.

The at least one physical variable can likewise be determined pixelwise by using MR fingerprinting.

In another embodiment of the method, the at least one physical variable can be one of the variables T1, T2, T2* or off resonance.

In a further embodiment of the method, after segmenting the image data of the examination object, healthy and pathological tissue can be determined manually and allocated to the image data. This allocation can then be supplied to the first and/or second database.

The MR system in accordance with the invention for segmenting image data of an examination object, has an MR scanner for acquiring raw data from an examination object. The scanner unit is connected to a processor that is configured to determine quantitative image data of the examination object and for segmenting the quantitative image data. The processor is connected to a display monitor that displays the parameters in a segmented display. The MR system is designed to carry out a method for segmenting image data of an examination object as described above.

The user of the inventive method and the associated device is therefore advantageously capable of carrying out segmenting processes of examination objects on the basis of quantitative MR images and of therefore avoiding the drawbacks of qualitative methods.

DESCRIPTION OF THE PREFERRED EMBODIMENTS

Figure 1:
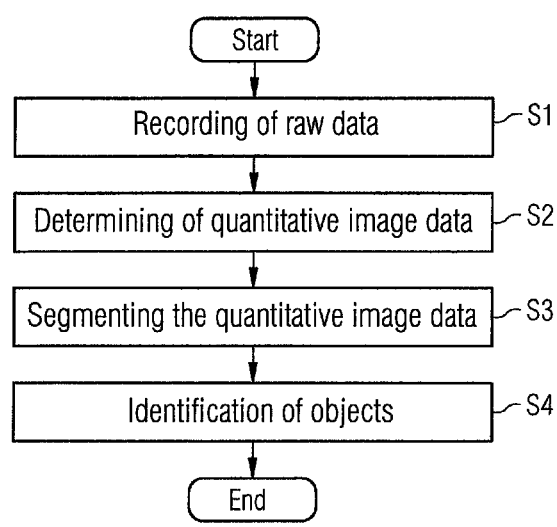
FIG. 1 is a flowchart of an embodiment of the inventive method for segmenting image data of an examination object.

FIG. 1 shows method steps for segmenting image data of an examination object. In the first step S1, the raw data of the examination object are acquired. The raw data include digitized MR signals that are produced during the scan sequence of the examination object. The signals are stored in a matrix (k-space) in a memory. The data stored in this way can be converted by a Fourier transformation for further processing.

The above-described raw data can include a large number of different items of information about the tissue. After the above-described transformation these items of information are available in the form of quantitative tissue parameters which are spatially and/or temporally resolved and include specific regions of the examination object or even the entire examination object.

These tissue parameters are combined in step S2 to form quantitative image data, it being possible for this to include for example T1, T2 or the spin density. T1 denotes the relaxation time of the longitudinal magnetization, i.e. the time after which the longitudinal magnetization has recovered to 63% of the original deflection which occurred due to the excitation pulse. T1 is specifically dependent on the type of bond of the hydrogen or water in the tissue, i.e. for example healthy tissue can be distinguished from diseased tissue using this parameter.

T2 denotes the relaxation time of the transverse magnetization, i.e. the time that elapses until the transverse magnetization has attained a specific divergence. T2 is based solely on spin-spin interactions and is not dependent on interactions with the environment. This parameter is therefore also tissue-specific.

To ascertain the quantitative image data from the MR signals a method can be applied which comprises the method of Magnetic Resonance Fingerprinting (MRF). In this case a pseudo-randomized signal characteristic is applied in an MR imaging method, with the different materials or tissue having a unique signal progression which simultaneously represents a function of the different material properties. After recording the signal characteristic a pattern recognition algorithm is applied to the data and converted into a quantitative visual representation. This is described for example in the article "Magnetic Resonance Fingerprinting" dated 14 Mar. 2013 495 (7440): 187-92.

In the following step S3, the quantitative image data are segmented in respect of at least one quantitative physical variable. Various methods can be used, which have the goal of identifying spatially related sections of the image and in this way of determining specific regions within the entire examination object and of contrasting these regions with the remainder of the examination object, i.e. the background.

For example, multi-stage segmenting methods exist that use a model-based segmenting approach that is expanded by higher dimensional input data. A segmenting hierarchy is used, with structures that are relatively easy to segment being segmented first. For example, bones can be easily segmented since bone tissue is conventionally better demarcated than, for example, cartilage. Models known as Active Shape Models (ASM) are used for this purpose.

The ASM can be expanded by the use of quantitative values (e.g. T1, T2) and the quality of the segmenting improved. Taking this as a starting point, the transition zone between bones and cartilage is identified with the aid of a statistical model of cartilage tissue.

Cartilage pixels thus can be identified in an iterative process with the use of a cartilage thickness model and local intensity edges in the image. Training data are used for the bone models from the ASM and the statistical cartilage models (mean thickness and variance).

In a preferred exemplary embodiment, the statistical model of the tissue (for example for cartilage) to be segmented is expanded by statistical variables (e.g. mean and variance) of the physical values relevant to the tissue to be segmented (in particular T2).

The inventive additional or sole use of input data with a number of quantitative physical variables helps to improve the accuracy of the models. The images to be segmented match the models better in their intensity distribution due to the improved reproducibility. Moreover, the use of a number of different physical variables increases the information content of the models and therewith the robustness in classification. As a result, for example during classification of the pixels, the weight of the cartilage, thickness model of the examination object, or other assumptions that go beyond individual pixels, can be reduced in favor of the scanned values of the individual pixels. This in turn improves the robustness of segmenting for cases with abnormal anatomy and in particular with pathologies.

In a further embodiment of the invention the physical values (e.g. T1, T2) are compared after segmenting with a database in which, from a large group of patients, normal ranges of the physical values are stored, so using these values a statement can be made about whether the quantitative values of the patient to be examined point toward a disease, an injury or a normal state. In addition, using normal values from databases specific tissue types, such as water, fat, muscle tissue, etc. can be allocated to the scanned regions.

In a further exemplary embodiment, the volumes determined from segmenting are compared with standard values from a database populated from a large number of people, in order to detect pathological changes early, for example a decrease in the cartilage volume or an increase in the synovial fluid in the case of arthrosis. This can be displayed as a graphic with a scan point and a normative region or as a colored overlay on the anatomical image.

After segmenting, the methods and exemplary embodiments can be used in a step S4 to identify predetermined objects. A user, for example a physician, can therefore display and evaluate the object identified in this way, and detect pathological structures in the object and distinguish them from healthy tissue.

In a further preferred embodiment of the method, after segmenting the quantitative image data and identification of the predetermined objects, for example of bones and muscle tissue, the quantitative image data and the signal characteristics in the muscle tissue can be viewed again and be divided into further fractions according to a method for MR fingerprinting subvoxel quantification. In the described method it is assumed that in certain previously segmented regions the signal is composed 100% of these fractions (here e.g. bones and muscle tissue), with the required quantitative tissue properties (T1, T2, . . . ) of the compartments being taken from a database or the literature.

In a further exemplary embodiment of the inventive method, an expanded segmenting method is performed using the at least one quantitative physical variable. The user can choose a specific pixel or region of the object, for example a tendon, with an algorithm searching, for example by means of a region growing method, the surrounding pixels for the same or similar quantitative values and in the case of a match allocating them to the same compartment. Starting from the matching pixels, the surrounding pixels are viewed again. In this way e.g. a tendon shall be followed up in order to detect it fully. In an advantageous form of presentation for example the three-dimensional characteristics of desired ligaments can be calculated for the user. By incorporating the above-mentioned segmenting in various tissue types the user can also be provided with an atlas-like anatomical presentation of an image in which specific tissue types and regions are marked in different colors and displayed three-dimensionally.

In a further aspect of the invention a reference database can be generated by calibration. In this case pathological and healthy cases are scanned, the image data recorded, retrospectively allocated by a physician to healthy or pathological tissue and then stored together with the scanned and allocated signal characteristics in a database. In this way tissue types whose differences have not yet been mapped in the models used for simulation and whose influence had potentially not yet been recognized can also be separated. One application that is of particular interest in orthopedics is the early detection of pathologies of cartilage tissue even before for example a change in volume occurs during the course of an arthrosis. In this connection it is also possible that longitudinal studies are evaluated and disease progression are correlated retrospectively with the changes in the quantitative scanned values or the signal characteristics, so threshold values can be derived therefrom that provide an early indication of a degenerative change.

In a further exemplary embodiment of the method, segmenting of specific tissue regions (for example fat, water, bones, cartilage, muscle, tendons, ligaments, menisci or edema) can occur using the at least one quantitative physical value, the segmenting can be done by thresholding, correlation analysis or statistical test methods.

In a further inventive embodiment of the method the described quantitative image data can also be used to be introduced into the reference database of physical values and into the reference database of the volume data of examination objects. This can occur in particular with the described calibrated data for different tissue types. The existing databases are thereby expanded by additional information and in conjunction with the above-described embodiments of the inventive method can deliver segmenting results with improved accuracy.

Furthermore, a segmenting method is proposed which, in addition to prior knowledge from the reference database about the geometry of the tissue to be segmented, also uses a statistical model for the at least one physical variable of the examination object. A probability is calculated that a pixel dependent on the physical variables quantitatively determined by MRF forms part of the tissue to be segmented.

In a further inventive embodiment, a quantitative ratio between at least two different physical variables of the predetermined object, for example fat/muscle or fat/water, can be determined and this ratio compared with normative data from the reference database which contains the physical variables of a large number of examination objects. Deviations can be displayed for example in the form of graphics or as a color chart or colored overlay over medical images or anatomical representations. The user can consequently easily visually detect changed or pathological tissue.

Figure 2:
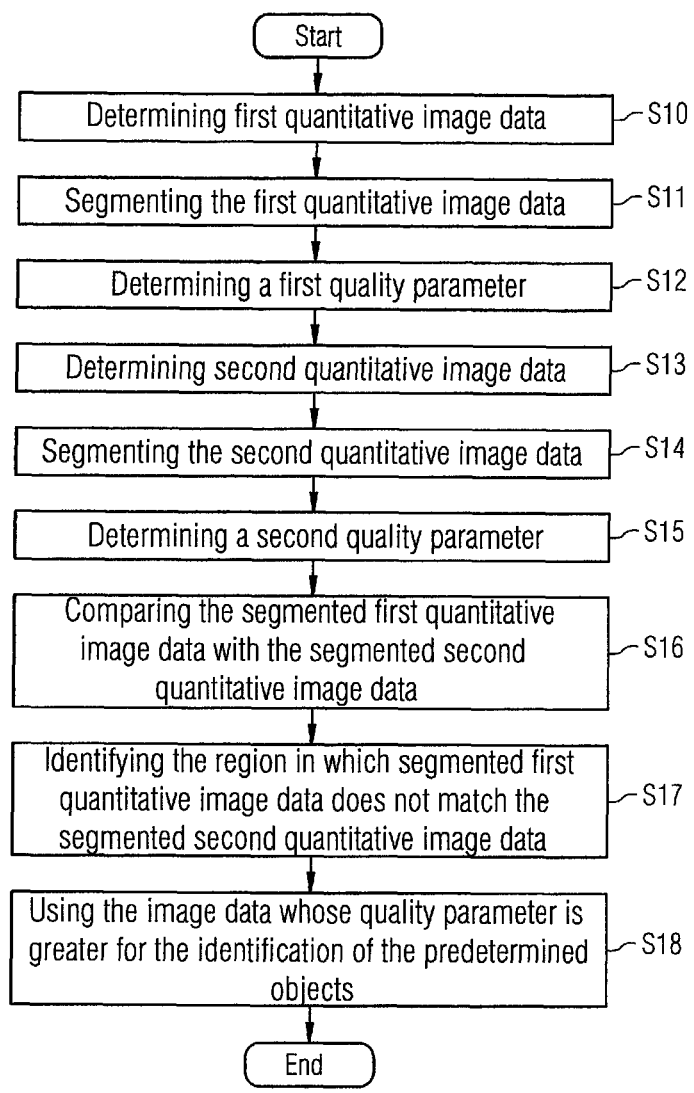
FIG. 2 is a flowchart of a further exemplary embodiment of the method for segmenting image data of an examination object.

FIG. 2 illustrates a further exemplary embodiment of the method in which at least two different quantitative physical variables are used to more accurately identify predetermined objects which can be identified inaccurately with only one quantitative physical variable. In a first step S10 a first set of quantitative image data is ascertained and a first physical variable determined and displayed. This can be, for example T1. Other parameters can likewise be used for this. In a second step S11 segmenting of the first image data then occurs. In a subsequent step S12 a first quality parameter is determined which describes how reliably the predetermined objects in the segmented first image data can be identified.

In a further step S13 a second set of quantitative image data is ascertained and a second physical variable determined and displayed. This can be for example T2, although the physical variable is not restricted thereto. The second image data is then segmented in a second step S14. A second quality parameter is then determined in a further step S15, and this describes how reliably the predetermined objects can be identified in the segmented second image data. The quality parameter can contain information about safety, specificity, probability or significance.

In a step S16, the first segmented quantitative image data is compared with the second segmented quantitative image data. If the identified objects in the segmented first quantitative image data and in the segmented second quantitative image data do not match in a specific region, this region is identified in a step S17. The image data whose quality parameter is greater is then used for identification of the predetermined objects in a step S18.

When executing the described method for example the method of Magnetic Resonance Fingerprinting (MRF) can be used, for example, preferably with at least two quantitative physical variables being scanned in a spatially resolved manner in a number of image series. A specific signal characteristic is generated voxelwise by pseudo-randomized characteristics of specific parameters in the MR imaging, i.e. scanned by predefined MRF protocols with pseudo-randomized characteristics of specific parameters, over a large number of images (N=1000-5000). This signal characteristic is called a fingerprint and with the aid of a database can be clearly allocated to a specific n-tuple of physical parameters, for example T1, T2, off resonance or MO. The fingerprint is thus a clear function of the material properties of the examination object.

For an automatic evaluation of a number of image series there is normally a need for registration since patient movements can occur during or between the scans. Registration algorithms for in practice often complex anatomies and non-rigid movements are often error-prone and computing-intensive. The use of multi-dimensional, simultaneously (i.e. with MRF for example) acquired image series avoids this otherwise present need for such a step if the acquisition method is sufficiently movement-insensitive.

In an exemplary embodiment, the spatially resolved determination of at least two quantitative physical variables can be used to overlay them computationally. For example, the variables T1 and T2 can be weighted according to the calculation rule $$\text{Overlaidimage} = n * T1\text{Map} + m * T2\text{Map},$$

for example where m=0.3 and n=10.

A substantially more accurate depiction of the object can therefore be achieved from quantitative image data, in which only one physical variable would generate too inaccurate a depiction of the predetermined object, by the combination and weighting of two different values.

Furthermore, in regions where the segmented first and second image data do not match sufficiently accurately, improved segmenting with mutual correction can be carried out using a comparison of the at least two segmenting results. For example, with a predetermined object in which one of the two physical variables has a higher specificity, the physical variable with the higher specificity is used when the image data of two physical parameters does not match.

In a further exemplary embodiment segmenting can be used to adjust individual implants and therewith for planning operations. For this the exact geometry of the bones to be replaced and that of the surrounding bone structure is obtained from the data. The preferably at least two quantitative values should be selected such that if possible the individual bone structure advantageously differs from the surroundings.

Figure 3:
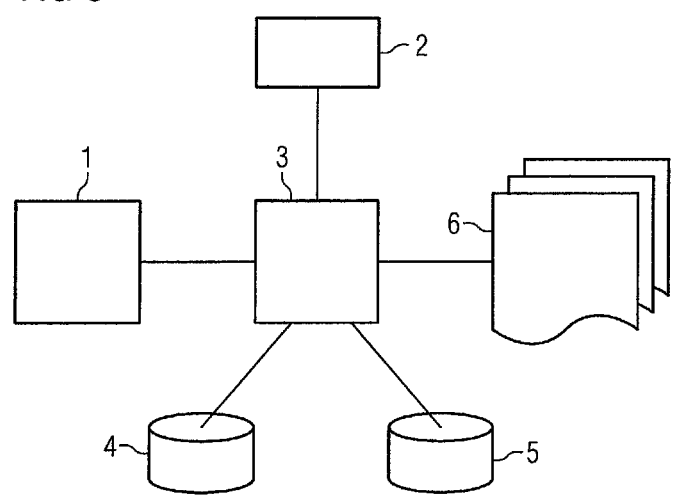
FIG. 3 schematically illustrates an MR system in accordance with the invention.

FIG. 3 illustrates an MR system for segmenting image data of an examination object. The system has a scanner 1 with which the examination object can be scanned and the raw data acquired. Various methods can be used, such as magnetic resonance fingerprinting.

The raw data are then supplied to a processor 3 that is connected to a memory 2. The raw data are stored in the memory 2 and are therefore available to the processor 3 for further processing. The processor 3 is designed to ascertain quantitative image data from the raw data, which can contain a large number of different physical variables of the examination object. The processor 3 can then apply different segmenting methods to the quantitative image data to ascertain segmented objects in this way. When using the segmenting method a reference database 4 is used that contains physical variables of a large number of examination objects. This is connected to the arithmetic unit. Furthermore, the processor 3 is connected to a further reference database 5 that contains volume data of a large number of examination objects. The two reference databases are used to make comparative reference data available to the algorithms in the segmenting method.

To be able to graphically display the segmented objects, the algorithms of the segmenting method can contain an image recognition algorithm which can be coupled to at least one of the reference databases 4, 5 which include known signal characteristics and physical variables of the examination object. The image recognition algorithm can compare the scanned signal characteristics with the data from the database and thereby generates segmented image displays of the desired objects. The objects segmented in this way are then displayed in a display monitor 6.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for segmenting image data of an examination object comprising:
   providing raw data to a computer, said raw data having been acquired from an examination object exhibiting at least one physical variable;
   in said computer, automatically determining quantitative image data of the examination object from the raw data and displaying said quantitative image data at a display screen in communication with said computer as a plurality of pixels with each pixel presenting a value of said at least one physical variable; in said computer, determining first quantitative image data from the raw data comprising pixels in which a value of a first physical variable is quantitatively ascertained, and displaying said pixels representing said first physical variable at said display screen;
   segmenting said first quantitative image data at said display screen to select at least one segment in the displayed quantitative image data that represents a predetermined image object in said quantitative image data;
   determining a first quality parameter for the segmented first image data that designates a degree of reliability that said predetermined image object can be identified in the segmented first image data;
   in said computer, determining second quantitative image data from the raw data comprising pixels in which a value of a second physical variable is quantitatively ascertained, and displaying said pixels representing said second physical variable at said display screen;
   segmenting said second quantitative image data at said display screen;
   determining a second quality parameter for the segmented second image data that designates a degree of reliability that said predetermined image object can be identified in the segmented second image data; and
   in said computer comparing the segmented first quantitative image data with the segmented second quantitative image data and, in any region in which the predetermined image object in the segmented first quantitative image data does not match the predetermined image object in the segmented second quantitative image data, automatically selecting, as said predetermined image object, the quantitative image data having a higher quality parameter associated therewith.

2. The method as claimed in claim 1 comprising, in said computer, determining an overlaid variable from said first and second physical variable of the examination object.

3. The method as claimed in claim 1 comprising implementing each segmenting using a statistical model of the examination object that is dependent on at least one statistical variable that is associated with said physical variable.

4. The method as claimed in claim 1 comprising determining said physical variable by magnetic resonance fingerprinting.

5. The method as claimed in claim 1 comprising employing, as said physical variable, a variable selected from the group consisting of T1, T2, T2* and off resonance in magnetic resonance imaging of said quantitative image data.

6. The method as claimed in claim 1 comprising, after segmenting said quantitative image data, manually allocating, via said display screen healthy and pathological tissue to said quantitative image data having said quality parameter associated therewith.

7. The method for segmenting image data of an examination object comprising:
   providing raw data to a computer, said raw data having been acquired from an examination object exhibiting at least one physical variable;
   in said computer, automatically determining quantitative image data of the examination object from the raw data and displaying said quantitative image data at a display screen in communication with said computer as a plurality of pixels with each pixel presenting a value of said at least one physical variable;
   segmenting the displayed quantitative image data to select at least one segment in the displayed quantitative image data that represents a predetermined image object in said quantitative image data; and
   comparing said physical variable in the quantitative image data of the predetermined image object with a reference database that comprises a plurality of sets of reference data respectively for different examination objects, and when a predetermined deviation of said physical variable from one of said reference data sets is exceeded, displaying a designation at said display screen that said deviation has been exceeded.

8. The method as claimed in claim 7 comprising, after segmenting the object in the quantitative image data, further segmenting said object by magnetic resonance fingerprinting sub-voxel quantification, using at least one physical variable of the pixels from said reference database.

9. The method as claimed in claim 8 comprising determining said predetermined image object by a procedure selected from the group consisting of thresholding, correlation analysis, region growing, image processing with regard to active objects, and statistical testing, of at least two physical variables in said quantitative image data by comparison with said first reference database.

10. The method as claimed in claim 9 wherein said reference database is a first reference database, and comprising, in said computer, determining a volume of said predetermined image object from said physical variable in the quantitative image data, and comparing said volume with a second reference database that comprises a plurality of sets of volume data respectively for different examination objects, and when a predetermined deviation of said volume from one of said volume data sets is exceeded, displaying a designation at said display screen that said deviation has been exceeded.

11. The method as claimed in claim 10 comprising supplying said quantitative data to at least one of said first reference database and said second reference database.

12. The method as claimed in claim 10 comprising allocating the quantitative image data to a tissue type and thereafter supplying said quantitative image data with said allocation to at least one of said first reference database and said second reference database.

13. The method as claimed in claim 12 comprising allocating said quantitative image data to said tissue type by selecting a pixel in said quantitative image data and then seeking adjacent pixels having a same quantitative value up to a predetermined deviation, and allocating said pixel and any of said pixels not exceeding said predetermined deviation to said tissue type.

14. The method as claimed in claim 7 comprising determining a quantitative ratio between at least two physical variables of said predetermined object and displaying a deviation of said quantitative ratio as at least one of a graphic, a color chart, or a color overlay on a medical image corresponding to said quantitative image data.

15. The method comprising:
providing raw data to a computer, said raw data having been acquired from an examination object exhibiting at least one physical variable;
in said computer, automatically determining quantitative image data of the examination object from the raw data and displaying said quantitative image data at a display screen in communication with said computer as a plurality of pixels with each pixel presenting a value of said at least one physical variable;
segmenting the displayed quantitative image data to select at least one segment in the displayed quantitative image data that represents a predetermined image object in said quantitative image data; and
in said computer, determining a volume of said predetermined image object from said physical variable in the quantitative image data, and comparing said volume with a reference database that comprises a plurality of sets of volume data respectively for different examination objects, and when a predetermined deviation of said volume from one of said volume data sets is exceeded, displaying a designation at said display screen that said deviation has been exceeded.

16. A magnetic resonance apparatus comprising:
a magnetic resonance scanner;
a computer configured to operate the magnetic resonance scanner to acquire raw data from an examination object in the magnetic resonance scanner, said examination object exhibiting at least one physical variable;
a display monitor in communication with said computer;
said computer being configured to automatically determine quantitative image data of the examination object from the raw data and to display said quantitative image data at said display monitor as a plurality of pixels with each pixel presenting a value of said at least one physical variable;
said computer being configured to segment the displayed quantitative image data to select at least one segment in the displayed quantitative image data that represents a predetermined image object in said quantitative image data; and
said computer being configured to compare said physical variable in said quantitative image data of the predetermined image object with a reference database that comprises a plurality of sets of reference data respectively for different examination objects, and when a predetermined deviation of said physical variable from one of said reference data sets is exceeded, displaying a designation at said display monitor that said deviation has been exceeded.

17. A magnetic resonance apparatus comprising:
a magnetic resonance scanner,
a computer configured to operate the magnetic resonance scanner to acquire raw data from an examination object in the magnetic resonance scanner, said examination object exhibiting at least one physical variable;
a display monitor in communication with said computer;
said computer being configured to automatically determine quantitative image data of the examination object from the raw data and to display said quantitative image data at said display monitor as a plurality of pixels with each pixel presenting a value of said at least one physical variable;
said computer being configured to segment the displayed quantitative image data to select at least one segment in the displayed quantitative image data that represents a predetermined image object in said quantitative image data; and
said computer being configured to determine a volume of said predetermined image object from said physical variable in the quantitative image data, and to compare said volume with a reference database that comprises a plurality of sets of volume data respectively for different examination objects, and when a predetermined deviation of said volume from one of said volume data sets is exceeded, displaying a designation at said display monitor that said deviation has been exceeded.

* * * * *